United States Statutory Invention Registration [19]

[11] Reg. Number: H962

Kovach [43] Published: Sep. 3, 1991

[54] AUTOMATED STABILITY/COMPATIBILITY APPARATUS

[75] Inventor: Lawrence J. Kovach, Bloomington, Ind.

[73] Assignee: United States of America, Washington, D.C.

[21] Appl. No.: 400,314

[22] Filed: Aug. 29, 1989

[51] Int. Cl.[5] ..... B01L 9/00; G05D 16/00

[52] U.S. Cl. ..... 422/68.1; 422/58; 422/104; 422/112; 435/291; 73/863.11; 73/864.91

[58] Field of Search ..... 422/58, 63, 64, 67, 422/68.1, 72, 100, 104, 112; 436/43, 45, 47, 51, 54; 435/289, 291; 73/863.11, 864.91, 865.5, 727; 604/45; 128/719; 250/282, 288

[56] References Cited

U.S. PATENT DOCUMENTS

| | | | |
|---|---|---|---|
| 3,941,566 | 3/1976 | Roche | 422/112 |
| 4,296,637 | 10/1981 | Calamur et al. | 73/863.11 |
| 4,322,980 | 4/1982 | Suzuki et al. | 73/727 |
| 4,411,158 | 10/1983 | Schaff, Jr. | 73/727 |
| 4,425,810 | 1/1984 | Simon et al. | 73/863.11 |
| 4,615,225 | 10/1986 | Sainz | 73/864.23 |
| 4,850,371 | 7/1989 | Broadhurst et al. | 604/45 |

*Primary Examiner*—Linda J. Wallace
*Attorney, Agent, or Firm*—William C. Townsend; Kenneth W. Dobyns; Edward J. Connors, Jr.

[57] ABSTRACT

Various samples of energetic materials are placed in multiple disposable culture tubes to simultaneously monitor and deterine their stability, reactivity, and compatibility. Each tube is evacuated and heated to accelerate aging of the samples, while a pressure transducer provides pressure readings inside the tube for computer analysis.

5 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

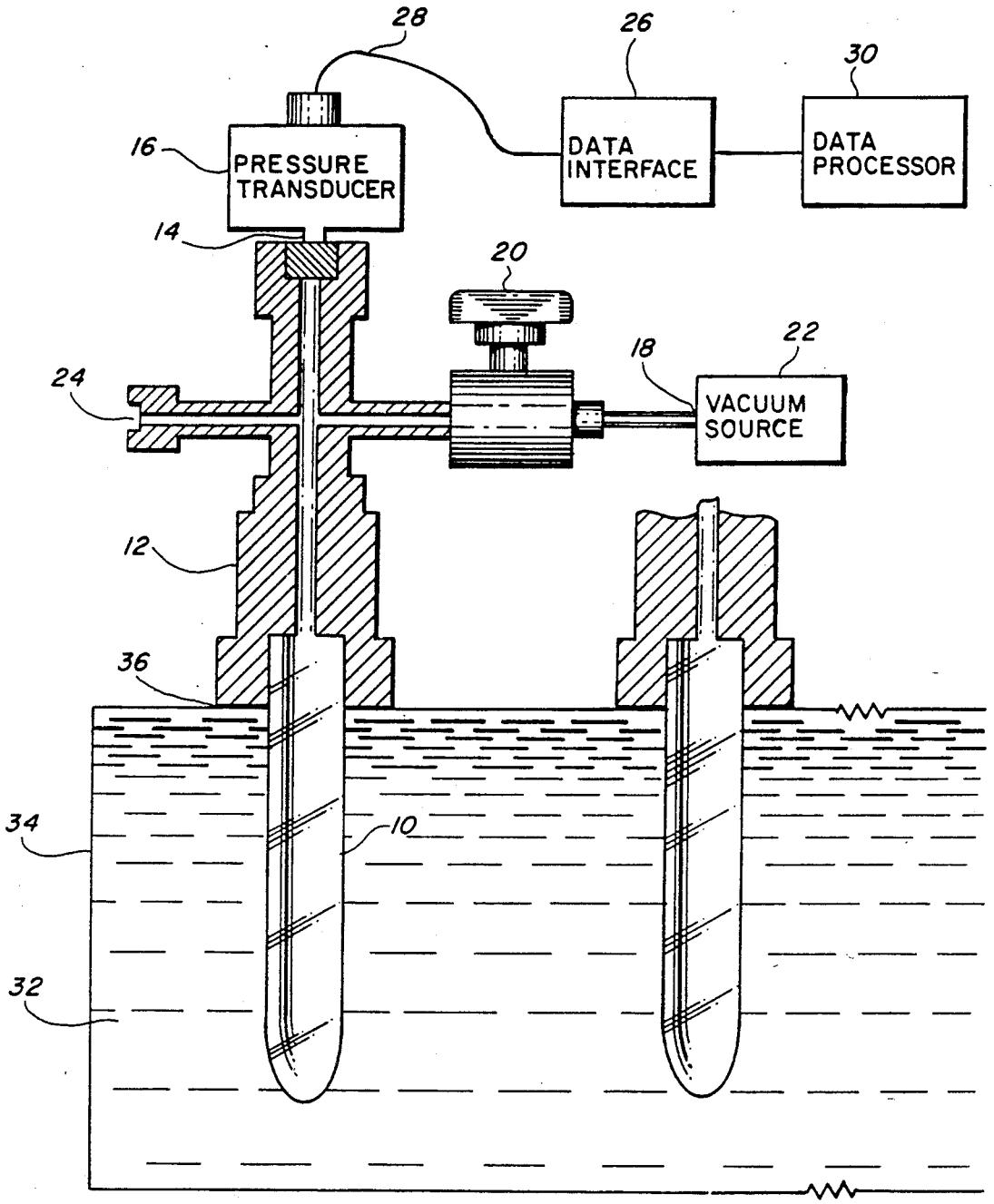
28
26
30
16
PRESSURE TRANSDUCER
DATA INTERFACE
DATA PROCESSOR
14
20
18
22
24
VACUUM SOURCE
12
36
34
10
32

AUTOMATED STABILITY/COMPATIBILITY APPARATUS

FIELD OF THE INVENTION

This invention relates to apparatus for measuring the physical properties of sample materials, and more particularly to apparatus for determining the stability and reactivity of energetic materials.

BACKGROUND OF THE INVENTION

In order to determine the stability, reactivity and compatibility of two or more materials, such as explosives, paints or adhesives, it is necessary to monitor the change of pressure of these materials over an extended period of time.

Current standard techniques employed to monitor such change of pressure utilize a mercury manometer connected to a sample tube. The materials are placed in a test tube which is fitted with a ground glass ball joint. A manometer tube is attached thereto via a mating ground glass ball joint. The reservoir on the other end of the manometer is filled with mercury. A vacuum source is attached to the tip of the manometer to permit evacuation of the interior of the assembly. After evacuation, the assembly is placed in a holding fixture with the test tube immersed in a heated bath at a preferred temperature of 100 degrees Centigrade.

The distance from the top of the mercury in the reservoir to the top of the column in the manometer capillary is measured and recorded, along with the ambient temperature and ambient pressure. At the end of a specified time, usually 40 hours, the mercury column height and ambient temperature and pressure are measured and recorded again. The change in internal gas volume is then calculated, corrected for standard temperature and pressure.

The data obtained by this technique provides only the change in internal gas volume over the duration of the test. The fragility of the manometer makes it a practical impossibility to measure the column height with any frequency. Moreover, the technique requires the handling of mercury in large quantities. Precision calibrated glassware needs to be repeatedly handled, including cleansing of melted energetic materials adhering to the test tube. Operating costs are high due to repeated cleaning requirements, the high cost of replacing breakable precision glassware, and the need to perform extensive and complicated calibration procedures on new glassware components.

OBJECTS OF THE INVENTION

It is therefore an object of the present invention to provide a system to determine and evaluate the stability and compatibility of energetic materials.

Another object of the present invention is to continuously monitor pressure changes of energetic materials in a heated, sealed system.

Yet another object of the present invention is to provide for a safe, efficient, accurate, and inexpensive device for monitoring the reactivity and stability of energetic materials.

Still another object of the present invention is to automatically analyze compatibility of numerous samples with reduced operator intervention.

A further object of the present invention is to evaluate explosive formulations and determine safety and hazard data.

Another object of the present invention is to measure physical properties of ordnance, propellants and pyrotechnic materials.

Still yet another object of the invention is the elimination of the need of the user to directly handle mercury when conducting compatibility tests.

In accordance with this invention, samples of material are placed in a test tube, which is then sealed to a manifold. The tube is evacuated and placed in a heated bath, with continuous pressure readings obtained and provided for computer analysis and evaluation. Gas chromotography and other forms of analysis may then be performed on the sample materials.

Further objects and advantages of the present invention will become apparent when reference is made to the following detailed description of the preferred embodiment of the invention and the accompanying drawing.

BRIEF DESCRIPTION OF THE DRAWING

The sole FIGURE shows a schematic representation of the automated compatibility apparatus according to this invention.

DESCRIPTION OF THE PREFERRED EMBODIMENT

Referring now to the FIGURE, there is shown a conventional culture tube 10, preferably of the disposable type. Sample energetic material or materials to be analyzed are prepared, measured to the required quantities, and inserted into tube 10. The open top of tube 10 is then inserted into the base of conventional stainless steel manifold 12 and clamped and sealed thereto.

Manifold 12 is provided with three output ports: Port 14 is fitted to a pressure transducer 16, port 18, provided with a sealing valve 20, to a vacuum source 22, and port 24 is coupled to diagnostic apparatus (not shown).

Pressure transducer 16 is coupled to conventional data interface 26 via cable 28. Data interface 26 is coupled to any desired data processor 30, such as a program operated computer which receives the output of transducer 16 in digital form. Vacuum source 22 is activated to evacuate the culture tube 10 to the desired internal pressure, at which point the vacuum source is removed from the system. Culture tube 10 is then placed into a heated bath 32, preferably a block 34 with a plurality of openings just slightly larger than the diameter of the tube 10 to enable numerous tubes to be simultaneously placed in the same heated bath. The base of manifold 12, designated as 36, supports tube 10 in the block 34.

The culture tube 10 is left in the bath 32 at the desired temperature for the requisite time period to accelerate the aging process of the samples contained therein. Throughout this time period, the output of pressure transducer 16 is provided in digital form to data processor 30 for continuous analysis and evaluation.

Data processor 30 is programmed to control data interface 26, read the pressure transducer 16 data, perform the calculations to convert the millivolt transducer readings to PSI at standard temperature and pressure relative to time zero, and store the data on disk. Additional programming may be added to perform other conversions, provide various forms of data output and provide options to match the needs of the application.

At the conclusion of the designated time period, the culture tube 10 is removed from the heated bath 32 and coupled to other equipment for post-aging gas analysis through port 24. Other suitable analytical equipment may be coupled through port 24, as desired.

The data obtained from computer 30 provides time/-pressure curves for the duration of the evaluation, providing data significantly more informative than two points of data developed by the prior art device. This data is automatically calculated and provided to the operator in text file, print, graphic display and any other desired format. This data illustrates the actual duration of the sample pre-heat, verifying the effects from fluctuations in ambient temperature and pressure, and providing information relevant to the aging process by indicating the possible pressure of multiple reaction mechanisms.

Thus, there has been provided durable, automated, diagnostic compatibility apparatus whose operating costs are minimal, requiring only the replacement of very inexpensive disposable culture tubes. Reduced operating expense, reduced operator intervention, the elimination of unnecessary handling and increased environmental safety are further advantages of the system. The system provides for continuous internal volume analysis, a practical method of observing pressure changes over the entire process.

The design of the manifold 12 permits easy connection to analytical equipment and the introduction of custom gas mixes or specific contaminants to observe their effects on the reactions present during the aging process.

The time/pressure curves and the ability to perform additional analysis on the aged material makes the apparatus highly applicable to areas of chemical stability and compatibility outside the field of energetic materials, including, for example, aging effects of polymers, compatibility of adhesives with substrate materials, and the effects of contaminants and specific atmospheres on micro-organism metabolism.

Having thus described the invention in full detail, it will be understood that these details need not be strictly adhered to but that various changes and modifications may suggest themselves to one skilled in the art, all falling within the scope of the invention as defined by the following claims.

I claim:

1. Apparatus for measuring the stability and compatibility of sample materials, comprising:

a container for receiving selected quantities of said materials, said container having an open top, a manifold for receiving said open top and sealing it therein, transducer means coupled to said manifold for measuring the pressure generated within said container by the aging process of the sample within said container and providing an output signal thereof, vacuum means coupled to said manifold for evacuating the interior of said container, computer means coupled to the output of said transducer for receiving data developed by said transducer, whereby when said container is heated to accelerate the aging process of the sample within said container, said transducer provides pressure data to said computer means, such that the stability and compatibility of said materials within said container may be determined.

2. Apparatus as recited in claim 1 wherein said container comprises a culture tube.

3. Apparatus as recited in claim 2 further comprising data interface means coupled between said transducer and said computer means.

4. Apparatus as recited in claim 2 further comprising a heated bath to heat the materials within said culture tube.

5. Apparatus as recited in claim 4 further comprising block means having multiple openings for receiving multiple culture tubes, said block means containing said heated bath.

* * * * *